United States Patent
Watanabe et al.

(10) Patent No.: US 10,295,461 B2
(45) Date of Patent: May 21, 2019

(54) TERAHERTZ TIME DOMAIN SPECTROSCOPY DEVICE

(71) Applicant: FEMTO Deployments Inc., Okayama-shi, Okayama (JP)

(72) Inventors: Akira Watanabe, Okayama (JP); Takeji Ueda, Okayama (JP); Tadashi Okuno, Okayama (JP)

(73) Assignee: FEMTO DEPLOYMENTS INC., Okayama (JP)

( * ) Notice: Subject to any disclaimer, the term of this patent is extended or adjusted under 35 U.S.C. 154(b) by 0 days.

(21) Appl. No.: 15/758,946

(22) PCT Filed: Oct. 18, 2016

(86) PCT No.: PCT/JP2016/080884
§ 371 (c)(1),
(2) Date: Mar. 9, 2018

(87) PCT Pub. No.: WO2017/069132
PCT Pub. Date: Apr. 27, 2017

(65) Prior Publication Data
US 2019/0041326 A1    Feb. 7, 2019

(30) Foreign Application Priority Data
Oct. 19, 2015 (JP) .................. 2015-205761

(51) Int. Cl.
*G01J 5/02* (2006.01)
*G01N 21/3586* (2014.01)
(Continued)

(52) U.S. Cl.
CPC ............ *G01N 21/3586* (2013.01); *G01J 3/42* (2013.01); *G01N 21/3577* (2013.01); *G01N 21/3581* (2013.01); *G01N 2201/06113* (2013.01)

(58) Field of Classification Search
CPC ........... G01N 21/3586; G01N 21/3577; G01N 2201/06113; G01J 3/42
See application file for complete search history.

(56) References Cited

U.S. PATENT DOCUMENTS 6,057,928 A * 5/2000 Li .................... G01N 21/41
356/445
6,828,558 B1 * 12/2004 Arnone .............. G01N 21/49
250/341.1
(Continued)

FOREIGN PATENT DOCUMENTS

JP    2006-064691 A    3/2006
JP    2008-083020 A    4/2008
(Continued)

OTHER PUBLICATIONS

Wang et al., "Ultrabroadband THz Time-Domain Spectroscopy of a Free-Flowing Water Film", IEEE Transaction on Terahertz Science and Technology, vol. 4, No. 4, Jul. 2014.
(Continued)

*Primary Examiner* — Kiho Kim
(74) *Attorney, Agent, or Firm* — Polsinelli PC

(57) ABSTRACT

There are provided a terahertz wave spectral dispersing unit 13 for spectrally dispersing a terahertz wave to be generated from a terahertz wave generating semiconductor 12 into two waves, a terahertz wave focusing unit 14 for focusing a terahertz wave transmitted through a sample liquid film 101 and a terahertz wave transmitted through a reference liquid film 102, and a terahertz wave detecting semiconductor 15 for detecting the focused terahertz wave, and it is possible to detect the terahertz wave transmitted through the sample liquid film 101 and the terahertz wave transmitted through the reference liquid film 102 in an interference state, thereby offsetting a noise made by a stripe-shaped wave generated
(Continued)

on the sample liquid film 101 and a noise made by a stripe-shaped wave generated on the reference liquid film 102.

12 Claims, 3 Drawing Sheets

(51) Int. Cl.
  *G01J 3/42* (2006.01)
  *G01N 21/3577* (2014.01)
  *G01N 21/3581* (2014.01)

(56) References Cited

U.S. PATENT DOCUMENTS

| | | | | |
|---|---|---|---|---|
| 6,957,099 | B1* | 10/2005 | Arnone | A61B 5/0059 |
| | | | | 250/330 |
| 9,835,552 | B2* | 12/2017 | Wagner | G01N 15/14 |
| 2002/0118371 | A1* | 8/2002 | Jiang | G01N 21/41 |
| | | | | 356/517 |
| 2004/0065832 | A1* | 4/2004 | Cluff | G01N 21/3581 |
| | | | | 250/341.1 |
| 2005/0100866 | A1* | 5/2005 | Arnone | A61B 5/0088 |
| | | | | 433/215 |
| 2006/0045807 | A1 | 3/2006 | Zhang et al. | |
| 2006/0226348 | A1 | 10/2006 | Abreu et al. | |
| 2008/0238571 | A1 | 10/2008 | Kurosaka | |
| 2008/0291463 | A1* | 11/2008 | Milner | A61B 1/00096 |
| | | | | 356/491 |
| 2009/0303480 | A1* | 12/2009 | Tamada | G01J 3/02 |
| | | | | 356/369 |
| 2012/0113417 | A1* | 5/2012 | Linfield | C30B 25/02 |
| | | | | 356/300 |
| 2014/0191131 | A1 | 7/2014 | Uchida et al. | |
| 2014/0198973 | A1* | 7/2014 | Zhang | G01J 3/42 |
| | | | | 382/149 |
| 2015/0136986 | A1* | 5/2015 | Akiyama | G01N 21/3581 |
| | | | | 250/339.06 |
| 2017/0010162 | A1* | 1/2017 | Shiramizu | G01B 9/02041 |
| 2017/0336259 | A1* | 11/2017 | Kawada | G01J 3/14 |
| 2017/0370833 | A1* | 12/2017 | Markelz | G01N 21/03 |

FOREIGN PATENT DOCUMENTS

| | | |
|---|---|---|
| JP | 2011-127950 A | 6/2011 |
| WO | WO-2012/165052 A1 | 12/2012 |
| WO | WO 2014/048799 A2 | 4/2014 |

OTHER PUBLICATIONS

Extended European Search Report dated Mar. 22, 2019 in European Appln. No. 16857445.7.
Skresanov et al., "Improved differential Ka band dielectrometer based on the wave propagation in a quartz cylinder surrounded by high loss liquid under test", Meas. Sci. Technol., 22(2011) 065403(9 pages).

* cited by examiner

TERAHERTZ TIME DOMAIN SPECTROSCOPY DEVICE

CROSS REFERENCE TO RELATED APPLICATIONS

This application is a National Phase filing under 35 U.S.C. § 371 of PCT/JP2016/080884 filed on Oct. 18, 2016; and this application claims priority to Application No. 2015-205761 filed in Japan on Oct. 19, 2015 under 35 U.S.C. § 119. The entire contents of each application are hereby incorporated by reference.

TECHNICAL FIELD

The present invention relates to a terahertz time-resolved spectroscopic device and more particularly, is suitably used for a device serving to arrange a liquid sample in a path through which a terahertz wave is propagated and serving to perform time domain spectroscopy measurement over a property of the terahertz wave transmitted through the liquid sample.

BACKGROUND ART

An electromagnetic wave is referred to as ultraviolet light, infrared light, a microwave, a terahertz wave or the like depending on a wavelength thereof. The technology for measuring various characteristics of a substance by using an electromagnetic wave is generally referred so as spectroscopic measurement or spectroscopy and a measuring device thereof is referred to as a spectroscopy device. Herein, a phenomenon which can be observed is greatly varied depending on a wavelength range of an electromagnetic wave to be used. For example, referring to a phenomenon of a molecule, it is possible to observe an electronic state for ultraviolet light, a vibration state for infrared light and a rotation state for a microwave, respectively.

Moreover, spectroscopy method is classified into absorption spectroscopy method or emission spectroscopy method depending on a physical quantity to be measured by an electromagnetic wave. The absorption spectroscopy method causes an electromagnetic wave to be incident on a sample and measures a physical property or chemical property of a sample based on a change in the electromagnetic wave which is caused by an interaction of the electromagnetic wave and the sample during passage through the sample or reflection thereof. The emission spectroscopy method emits an electromagnetic wave from the sample by any method and measures a strength of the electromagnetic wave.

In order to measure how to vary a physical quantity to be measured with passage of time, time domain spectroscopy is performed. The time domain spectroscopy method serves to measure a transient spectrum by using the ultrashort pulse laser, thereby enabling observation of a state in which even a very quick reaction on a Femtosecond level progresses. Terahertz time domain spectroscopy method serves to perform Fourier transformation over a time waveform of an electromagnetic wave to be obtained by directly measuring a waveform of a terahertz wave, thereby acquiring information about an amplitude and a phase of the terahertz wave.

A substance to be measured which is a spectroscopic measuring target includes gaseous, solid-state and liquid-state configurations and the like. Depending on the respective configurations, there is devised a method of installing a substance to be measured in such a manner that an electromagnetic wave is transmitted properly. In order to perform measurement with high precision over a liquid-state sample, for instance, a sample to be arranged as a measured target in a spectroscopy device is required to be formed so thinly that an electromagnetic wave is transmitted, and furthermore, is to be installed in such a manner that impurities other than a substance to be measured is not mixed therein. In the case in which a liquid sample is subjected to spectroscopic measurement with a terahertz wave, particularly, it is necessary to perform the measurement by making a liquid into a plate-shaped uniform thin film and transmitting a terahertz wave through the plate-shaped part in order to prevent a reduction in an SN ratio of a measuring signal to be detected because of a great absorption effect for the terahertz wave through a water molecule.

In the measurement for a liquid sample, generally, the sample is inserted into a vessel (generally referred to as a solution cell) formed by a material for transmitting an electromagnetic wave, for example, glass and the electromagnetic wave is incident from an outside of the solution cell to measure the electromagnetic wave transmitted through the solution cell. When the liquid sample is inserted into the solution cell and is thus measured, however, spectroscopic information of a cell material is superimposed as a noise on a measuring signal with respect to spectroscopic information of the liquid sample so that the measurement for true spectroscopic information is disturbed.

In consideration of such a problem, conventionally, there is proposed a liquid thinning device which is intended for enabling measurement of spectroscopic information with small noises without using a solution cell (for example, see Patent Document 1). The liquid thinning device described in the Patent Document 1 serves to directly make a liquid sample thin-film shaped by using the nozzle and make a surface wave through a sound wave or an ultrasonic wave on a surface of a liquid film to be generated by a nozzle, thereby reducing a flatness of a liquid film surface and removing an interference of an electromagnetic wave which is a defect of the nozzle.

Patent Document 1: Japanese Laid-Open Patent Publication No. 2011-127950

DISCLOSURE OF THE INVENTION

Referring to the Patent Document 1, if the surface of the liquid-state thin film to be generated by the nozzle is very flat, a multiple interference between a surface of a liquid film and a back face thereof is caused so that a noise is made. In order to prevent this state, therefore, a sound wave or an ultrasonic wave is generated on the surface of the liquid film. However, it is very hard to form a completely flat liquid-state thin film by the nozzle really. In some cases, actually, a stripe-shaped wave is generated on the liquid film surface. In the case in which a size of the stripe-shaped wave is almost equal to a wavelength of a terahertz wave, an interference effect is produced and a noise caused thereby is superimposed on a measuring signal.

In general, a band of a terahertz wave to be used for measurement in terahertz time domain spectroscopy is approximately 1 to 3 THz. The terahertz wave has a wavelength of 300 microns with 1 THz and a wavelength of 100 microns with 3 THz. In this case, a stripe-shaped wave appearing on the surface of the liquid film to be generated by the nozzle has a dimension which is almost equal to the wavelength of the terahertz wave to be used for the measurement. For this reason, a noise is made by an interference.

If a pump is used as a power source for jetting a liquid from a nozzle, moreover, a peculiar pulsation from the pump is generated so that a vibration is created over a liquid to be sent out. The vibration of the liquid is also transmitted to a liquid film to be formed by jetting the liquid from the nozzle so that a stripe-shaped wave generated on a liquid film is also vibrated. As a result, a terahertz wave passed through the liquid film is brought into a situation in which a wave having an equal dimension to its own wavelength is practically passed through a vibrated mesh. Consequently, the noise is inevitably superimposed on a measuring signal.

The present invention has been made to solve the problem and has an object to enable suppression of superimposition of a noise which is caused by an interference of a stripe-shaped wave appearing on a surface of a liquid-state thin film to be generated by a nozzle and a terahertz wave and measurement of true spectroscopic information of a liquid sample with high sensitivity.

In order to attain the object, the present invention spectrally disperses, into two waves, a terahertz wave to be generated from a terahertz light source and causes one of the terahertz waves to be transmitted through a sample liquid film and the other terahertz wave to be transmitted through a reference liquid film, and focuses the respective terahertz waves transmitted through the sample liquid film and the reference liquid film and detects the focused terahertz wave.

According to the present invention having the structure described above, the terahertz wave transmitted through the sample liquid film and the terahertz wave transmitted through the reference liquid film are detected in an interference state. Therefore, it is possible to offset a noise made by a stripe-shaped wave generated on the sample liquid film and a noise made by a stripe-shaped wave generated on the reference liquid film. At this time, if the sample liquid film and the reference liquid film are formed by the same liquid, true spectroscopic information of the sample liquid film is also offset by true spectroscopic information of the reference liquid film. On the other hand, if the sample liquid film has a different property from the reference liquid film, spectroscopic information other than the different property are offset. Consequently, only spectroscopic information about the different property, that is, a characteristic property of the sample liquid film is detected. According to the present invention, thus, it is possible to suppress superimposition of a noise caused by the interference of a stripe-shaped wave appearing on the surface of the liquid film and a terahertz wave, thereby measuring the true spectroscopic information of the liquid sample with high sensitivity.

BEST MODE FOR CARRYING OUT THE INVENTION

Figure 1:
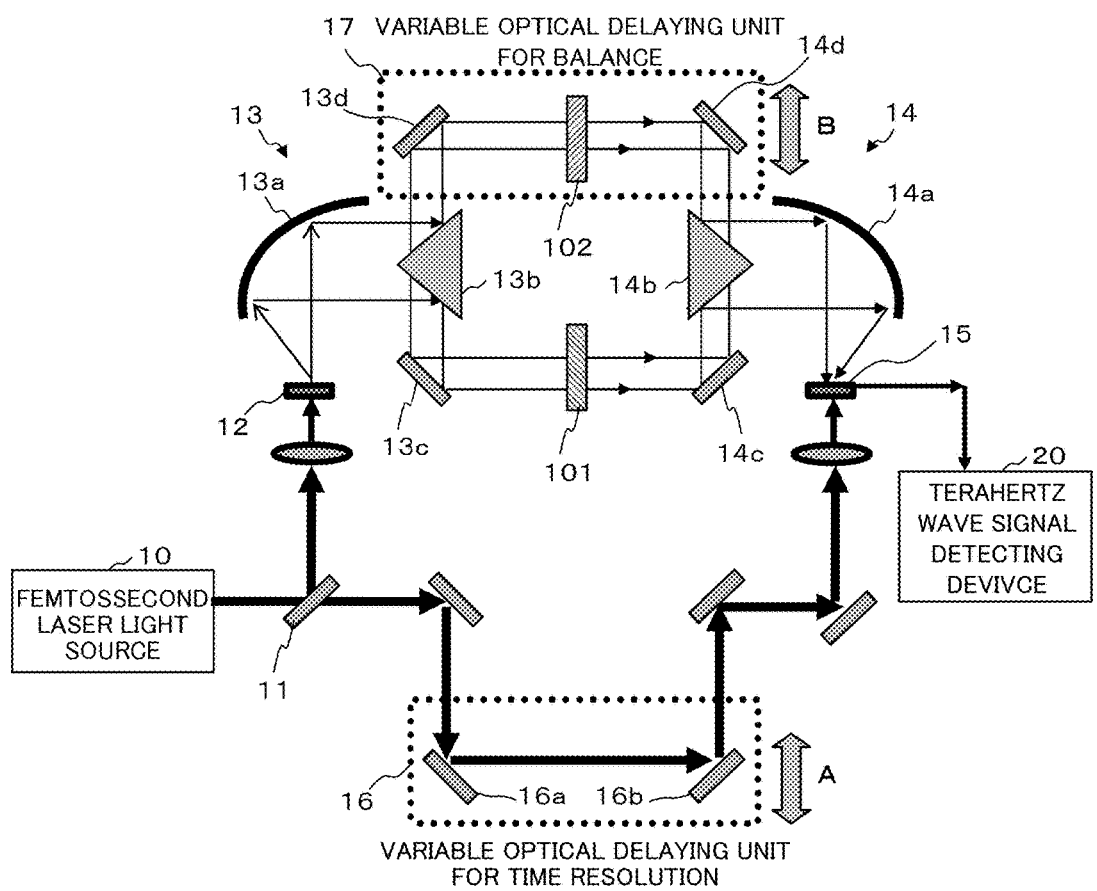
FIG. 1 is a diagram showing an example of a structure of a terahertz time domain spectroscopy device according to the present embodiment.

An embodiment of the present invention will be described below with reference to the drawings. FIG. 1 is a diagram showing an example of a structure of a terahertz time domain spectroscopy device according to the present embodiment. The terahertz time domain spectroscopy device according to the present embodiment serves to arrange a liquid sample in a path through which a terahertz wave is propagated and to perform time domain spectroscopy measurement over a property of the terahertz wave transmitted through the liquid sample. Specifically, a time waveform of the terahertz wave transmitted through the liquid sample is detected and a detection signal is subjected to Fourier transformation to obtain information about an amplitude and a phase for each frequency of the terahertz wave. A Femtosecond laser pulse to be excitation light is used as a light source.

As shown in FIG. 1, the terahertz time domain spectroscopy device according to the present embodiment includes a Femtosecond laser light source 10, a laser light spectral dispersing unit 11, a terahertz wave generating semiconductor 12 (corresponding to a terahertz light source in claims), a terahertz wave spectral dispersing unit 13, a terahertz wave focusing unit 14, a terahertz wave detecting semiconductor 15 (corresponding to a terahertz wave detecting unit in claims), a variable optical delaying unit 16 for time resolution, a variable optical delaying unit 17 for balance (corresponding to a variable optical delaying unit in claims) and a terahertz signal detecting device 20.

The laser light spectral dispersing unit 11 divides laser light (a Femtosecond laser pulse) to be emitted from the Femtosecond laser light source 10 into two waves including pump light for operating the terahertz wave generating semiconductor 12 serving as a terahertz light source and sampling light for increasing weak current to be created by a terahertz wave which is incident on the terahertz wave detecting semiconductor 15 serving as a terahertz wave detecting unit. Specifically, the laser light spectral dispersing unit 11 is configured from a semitransparent mirror.

The terahertz wave spectral dispersing unit 13 spectrally disperses a terahertz wave to be generated from the terahertz wave generating semiconductor 12 into two waves. Specifically, the terahertz wave spectral dispersing unit 13 is configured from a parabolic mirror 13a, a triangular prism 13b, and two reflection mirrors 13c and 13d.

The terahertz wave generated from the terahertz wave generating semiconductor 12 is reflected by the parabolic mirror 13a and is output as a parallel bundle of rays without an aberration. A terahertz wave to be the bundle of rays is reflected by two planes of the triangular prism 13b respectively and is spectrally dispersed into two directions. The terahertz wave dispersed spectrally into one of the directions is reflected by the reflection mirror 13c and is transmitted through a sample liquid film 101. The terahertz wave dispersed spectrally into the other direction is reflected by the reflection mirror 13d and is transmitted through a reference liquid film 102. The sample liquid film 101 and the reference liquid film 102 will be described below in detail.

The terahertz wave focusing unit 14 focuses the terahertz wave transmitted through the sample liquid film 101 and the terahertz wave transmitted through the reference liquid film 102. Specifically, the terahertz wave focusing unit 14 is configured from a parabolic mirror 14a, a triangular prism 14b and two reflection mirrors 14c and 14d.

One of the terahertz waves which is transmitted through the sample liquid film 101 is sequentially reflected by the reflection mirror 14c and the triangular prism 14b, and is then incident on the parabolic mirror 14a. On the other hand, the other terahertz wave transmitted through the reference liquid film 102 is sequentially reflected by the reflection mirror 14d and the triangular prism 14b and is then incident on the parabolic mirror 14a. The parabolic mirror 14a collects a bundle of rays incident in parallel from the triangular prism 14b (a bundle of the terahertz waves transmitted through the sample liquid film 101 and the terahertz waves transmitted through the reference liquid film 102) onto a focal point of the terahertz wave detecting semiconductor 15 without an aberration.

The terahertz wave detecting semiconductor 15 detects the terahertz wave focused by the terahertz wave focusing unit 14 and outputs a terahertz wave signal representing a waveform thereof. The terahertz signal detecting device 20 detects the terahertz wave signal and performs the Fourier transformation over the detection signal, thereby acquiring information about an amplitude and a phase for each frequency of the terahertz wave.

The variable optical delaying unit 16 for time resolution is provided in a path through which sampling light to be either laser light obtained by the laser light spectral dispersing unit 11 is propagated and variably sets a delay quantity of the sampling light. The variable optical delaying unit 16 for time resolution has two reflection mirrors 16a and 16b, and the reflection mirrors 16a and 16b are configured so as to be physically movable in parallel in a direction of an arrow A. Consequently, a delay time of the sampling light is made variable. The variable optical delaying unit 16 for time resolution is used for measuring a time variation in a terahertz wave while shifting a timing in which the sampling light reaches the terahertz wave detecting unit 15.

The variable optical delaying unit 17 for balance is provided on a path through which either of two terahertz waves that is obtained by the terahertz spectral dispersing unit 13 and is transmitted through the reference liquid film 102 is propagated, and serves to variably set a delay quantity of the terahertz wave. The variable optical delaying unit 17 for balance has the two reflection mirrors 13d and 14d and has a structure in which the reflection mirrors 13d and 14d are physically movable in parallel in a direction of an arrow B. The variable optical delaying unit 17 for balance is used for regulating the delay quantity of the terahertz wave at the reference liquid film 102 side so as to balance the terahertz waves divided into two waves through the terahertz wave spectral dispersing unit 13 without a difference in an optical path including a liquid film.

Figure 2:
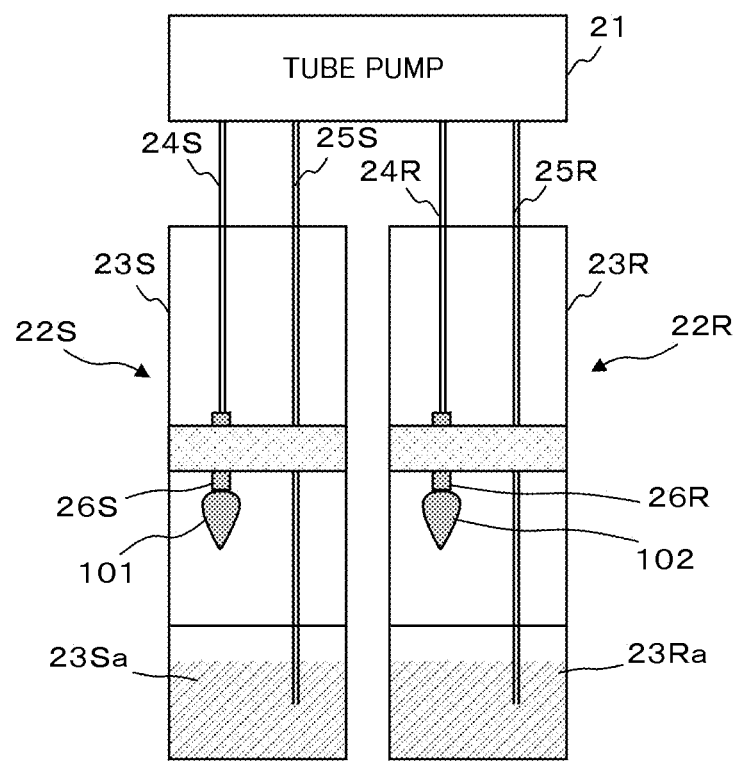
FIG. 2 is a diagram showing an example of a structure of a liquid circulating device for generating a liquid film according to the present embodiment.

FIG. 2 is a diagram showing an example of a structure of a liquid circulating device for generating the sample liquid film 101 and the reference liquid film 102. As shown in FIG. 2, the liquid circulating device according to the present embodiment includes a tube pump 21, a sample liquid film generating unit 22S for generating the sample liquid film 101 by using a measuring target liquid, and a reference liquid film generating unit 22R for generating the reference liquid film 102 by using a liquid for reference.

The sample liquid film generating unit 22S includes a vessel 23S, an outgoing pipe 24S, a returning pipe 25S and a nozzle 26S. The vessel 23S is provided with a liquid tank 23Sa. Similarly, the reference liquid film generating unit 22R includes a vessel 23R, an outgoing pipe 24R, a returning pipe 25R and a nozzle 26R. The vessel 23R is provided with a liquid tank 23Ra. Thus, the sample liquid film generating unit 22S and the reference liquid film generating unit 22R have completely the same structures and are the same on a structure and mechanism basis.

The tube pump 21 sucks up a measuring target liquid through the returning pipe 25S from the liquid tank 23Sa of the sample liquid film generating unit 22S and derives the liquid sucked up to the nozzle 26S through the outgoing pipe 24S. The liquid is then jetted from the nozzle 26S so that the sample liquid film 101 is formed. The sample liquid film 101 is changed into a water droplet, and the water droplet is stored in the liquid tank 23Sa and is sucked up again by the tube pump 21.

Moreover, the tube pump 21 sucks up a liquid for reference from the liquid tank 23Ra of the reference liquid film generating unit 22R through the returning pipe 25R and derives the liquid sucked up to the nozzle 26R through the outgoing pipe 24R. Then, the liquid is jetted from the nozzle 26R so that the reference liquid film 102 is formed. The reference liquid film 102 is changed into a water droplet, and the water droplet is stored in the liquid tank 23Ra and is sucked up again by means of the tube pump 21.

Thus, the liquid in the liquid tank 23Sa is circulated in the sample liquid film generating unit 22S and the sample liquid film 101 is formed by the nozzle 26S in the circulation process. Moreover, the liquid in the liquid tank 23Ra is circulated in the sample liquid film generating unit 22R and the reference liquid film 102 is formed by the nozzle 26R in the circulation process. Both the sample liquid film 101 and the reference liquid film 102 have liquid film surfaces on which stripe-shaped waves are generated. Furthermore, the stripe-shaped wave is vibrated upon influence of a peculiar pulsation to the tube pump 21.

In the present embodiment, there is provided the reference liquid film generating unit 22R having the same structure as the sample liquid film generating unit 22S, and the terahertz wave divided into two waves by the terahertz wave spectral dispersing unit 13 is transmitted through both the sample liquid film 101 and the reference liquid film 102 and is then focused and detected. Consequently, a noise to be superimposed on a measuring signal by the vibrated stripe-shaped wave can be offset.

Specifically, the same liquid are stored in the liquid tank 23Sa of the sample liquid film generating unit 22S and the liquid tank 23Ra of the reference liquid film generating unit 22R, and are sucked up by the single tube pump 21 and are thus circulated so that the sample liquid film 101 and the reference liquid film 102 are formed. Then, the terahertz wave transmitted through the sample liquid film 101 and the reference liquid film 102 is detected by the terahertz wave detecting semiconductor 15 and a terahertz wave signal to be output from the terahertz wave detecting semiconductor 15 is detected by the terahertz signal detecting device 20.

At this time, by operating the variable optical delaying unit 17 for balance which is added to an optical path of a terahertz wave on the reference liquid film 102 side, it is possible to perform regulation so as to eliminate a difference in the optical path including the liquid film between the terahertz wave on the sample liquid film 101 side and the terahertz wave on the reference liquid film 102 side. In other words, by operating the variable optical delaying unit 17 for balance to vary the delay quantity of the terahertz wave on the reference liquid film 102 side, it is possible to perform regulation in such a manner that the terahertz wave signal to be detected by the terahertz signal detecting device 20 is zero.

In a situation in which the terahertz wave signal is zero, thus, the terahertz wave transmitted through the sample liquid film 101 and the terahertz wave transmitted through the reference liquid film 102 are balanced. By using a different liquid from the reference liquid to be stored in the liquid tank 23Ra of the reference liquid film generating unit 22R as a sample liquid to be stored in the liquid tank 23Sa of the sample liquid film generating unit 22S while maintaining the state of the variable optical delaying unit 17 for balance which creates the balance situation, accordingly, it is possible to detect a difference from the balance state very sensitively.

In other words, the sample liquid film 101 and the reference liquid film 102 are formed by using the same liquid and the state in which the terahertz waves transmitted through both of the liquid films 101 and 102 are balanced is created, and the measuring target liquid is then stored in the liquid tank 23Sa of the sample liquid film generating unit 22S and the sample liquid film 101 is formed to transmit the terahertz wave therethrough. Consequently, it is possible to sensitively detect spectroscopic information representing a peculiar property to the measuring target liquid as a difference in the property of the terahertz wave transmitted through the reference liquid film 102 while a noise to be superimposed on a measuring signal by the vibrated stripe-shaped wave is offset.

For example, by storing a drink product immediately after manufacture in the liquid tank 23Ra of the reference liquid film generating unit 22R and storing the returned drink product in the liquid tank 23Sa of the sample liquid film generating unit 22S to perform terahertz time-resolved spectroscopic measurement, it is possible to detect true spectroscopic information representing a peculiar property to the returned drink product without influence of a noise made by the stripe-shaped wave generated on the sample liquid film 101. If a molecule of any toxic substance is mixed in the returned drink product, for example, it is possible to sensitively detect, as a terahertz wave signal, spectroscopic information originated from the toxic substance.

It is preferable that the structure shown in FIG. 1 (at least the structure of a path portion from the terahertz wave generating semiconductor 12 to the terahertz wave detecting semiconductor 15) and the structure shown in FIG. 2 should be covered with a vacuum vessel and a terahertz wave to be generated by the terahertz wave generating semiconductor 12 should be propagated in vacuum. Moreover, it is preferable that the vessels 23S and 23R should be configured by a transparent material (polypropylene, polyethylene, glass or the like) to the terahertz wave. Furthermore, it is further preferable to provide, on terahertz wave paths of the vessels 23S and 23R, beam passage holes through which terahertz waves pass.

As described above in detail, in the present embodiment, the terahertz wave to be generated from the terahertz wave generating semiconductor 12 is divided into two waves by the terahertz wave spectral dispersing unit 13, and one of the terahertz waves is transmitted through the sample liquid film 101 and the other terahertz wave is transmitted through the reference liquid film 102, and the respective terahertz waves transmitted through the sample liquid film 101 and the reference liquid film 102 are focused and detected by the terahertz wave detecting semiconductor 15.

According to the present embodiment having such a structure, the terahertz wave transmitted through the sample liquid film 101 and the terahertz wave transmitted through the reference liquid film 102 are detected in an interference state. Therefore, it is possible to offset a noise made by the stripe-shaped wave generated on the sample liquid film 101 and a noise made by the stripe-shaped wave generated on the reference liquid film 102. At this time, if the sample liquid film 101 has a different property from the reference liquid film 102, spectroscopic information other than the different property are offset so that the different property, that is, only spectroscopic information related to a characteristic property of the sample liquid film 101 is detected. According to the present embodiment, consequently, it is possible to suppress superimposition of noises caused by the interference of the stripe-shaped wave appearing on the surface of the liquid film and the terahertz wave, thereby measuring true spectroscopic information of the liquid sample with high sensitivity.

Figure 3:
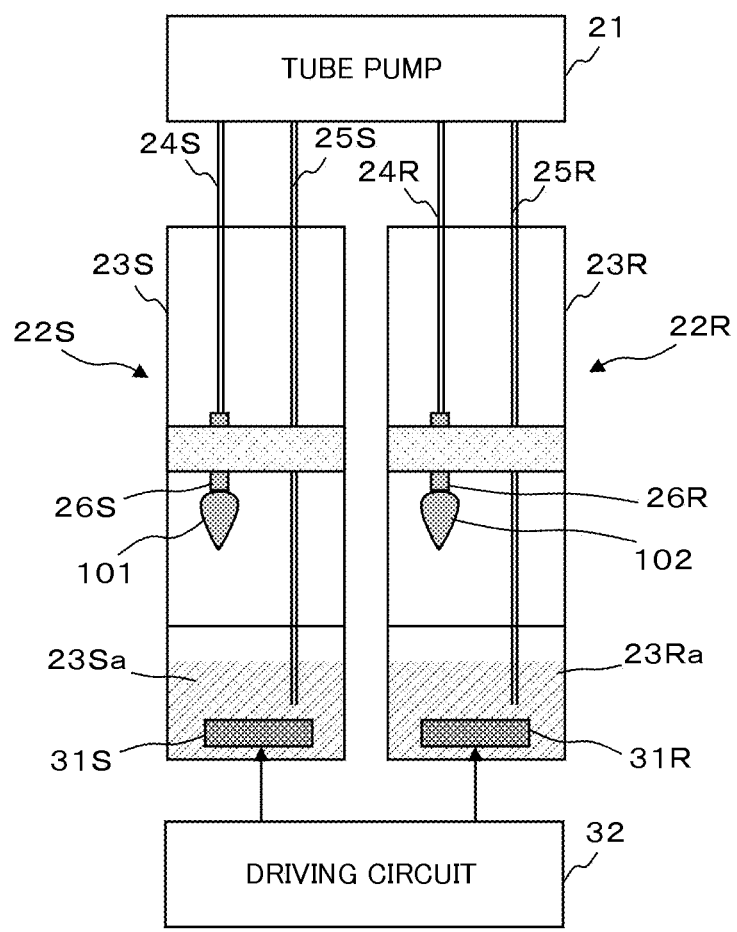
FIG. 3 is a diagram showing another example of the structure of the liquid circulating device for generating a liquid film according to the present embodiment.

FIG. 3 is a diagram showing another example of the structure of the liquid circulating device. In FIG. 3, components having the same functions as the components shown in FIG. 2 have the same reference numerals. The liquid circulating device shown in FIG. 3 further includes a temperature control unit for applying a thermal disturbance to the liquid in each of the liquid tanks 23Sa and 23Ra in addition to the structure shown in FIG. 2. The temperature control unit is configured from heating/cooling elements 31S and 31R, and a driving circuit 32 for driving the heating/cooling elements 31S and 31R. The heating/cooling elements 31S and 31R can be configured from Peltier elements, for example.

The stripe-shaped wave is generated on the liquid film surfaces of the sample liquid film 101 and the reference liquid film 102 because of a turbulent flow of a liquid to be formed at an outlet of the nozzle 26. The turbulent flow of the liquid to be jetted from a small hole of the nozzle 26 is related to a viscosity of the liquid to be jetted from the hole of the nozzle 26. In other words, the turbulent flow of the liquid is more reduced with an increase in the viscosity of the liquid. The viscosity of the liquid greatly depends on a temperature of the liquid. In other words, the viscosity is increased with a reduction in the temperature of the liquid.

The liquid circulating device shown in FIG. 3 can increase the viscosity of the liquid by reducing the temperature of the liquid in each of the liquid tanks 23Sa and 23Ra with use of the heating/cooling elements 31S and 31R. As a result, it is possible to reduce the generation of the stripe-shaped waves on the sample liquid film 101 and the reference liquid film 102 by decreasing the turbulent flow of the liquid to be jetted from the nozzle 26. If the striped-shaped waves to be generated on the sample liquid film 101 and the reference liquid film 102 are lessened, a noise offset effect produced by a balance of optical systems is also enhanced.

For example, in the case in which a drink product such as juice or tea which has a comparatively low viscosity is set to be a measuring target, it is possible to reduce the stripe-shaped waves to be generated on the sample liquid film 101 and the reference liquid film 102, thereby enhancing the noise offset effect through the balance of the optical systems by dropping the temperature of the liquid in each of the liquid tanks 23Sa and 23Ra with use of the heating/cooling elements 31S and 31R as described above.

On the other hand, the liquid to be the measuring target also contains a liquid having a very high viscosity, for example, olive oil, emulsion (cosmetics) or the like. In this case, if the liquid circulating device is configured by using the tube pump 21 having a maximum pressurizing force which is not very high, the pressurizing force of the tube pump 21 sometimes lacks with respect to the liquid having a high viscosity. In this case, by raising the temperature of the liquid in each of the liquid tanks 23Sa and 23Ra with use of the heating/cooling elements 31S and 31R, it is possible to reduce the viscosity of the liquid, thereby circulating the liquid within the working range of the tube pump 21.

As described above, by controlling the temperature of the liquid in each of the liquid tanks 23Sa and 23Ra with use of the heating/cooling elements 31S and 31R, it is possible to reduce the generation of the stripe-shaped wave or to contain a pressurizing range required for the tube pump 21 into a certain range. Therefore, it is possible to construct a versatile liquid circulating device without requiring to perform exchange into the nozzle 26 having a different opening dimension or exchange into the tube pump 21 having a different pressurizing capability depending on the viscosity of the liquid to be the measuring target.

In the case in which a pump having a sufficiently high pressurizing capability is used, it is also possible to use a cooling element capable of performing only cooling in place of the heating/cooling elements 31S and 31R.

Although the description has been given to the example in which the variable optical delaying unit 17 for balance is provided on the optical path at the side where the terahertz wave is transmitted through the reference liquid film 102 in the embodiment, the variable optical delaying unit 17 for balance may be provided on an optical path at the sample liquid film 101 side. Alternatively, the variable optical delaying unit 17 for balance may be provided on both the optical path at the sample liquid film 101 side and the optical path at the reference liquid film 102 side.

Although the description has been given to the example in which the delay quantity of the terahertz wave is regulated by the variable optical delaying unit 17 for balance in the embodiment, moreover, it is also possible to further include a liquid film moving unit for moving an arrangement position of the reference liquid film 102 corresponding to the movement of the reflection mirrors 13d and 14d possessed by the variable optical delaying unit 17 for balance. For example, it is possible to configure the liquid film moving unit by constituting the nozzle 26R so as to be physically movable in parallel in the direction of the arrow B. In the case in which the variable optical delaying unit 17 for balance is provided on the optical path at the sample liquid film 101 side, the nozzle 26S is configured to be physically movable in parallel.

Although the description has been given to the example in which the variable optical delaying unit 16 for time resolution is arranged in the path through which the sampling light is propagated in the embodiment, moreover, the variable optical delaying unit 16 for time resolution may be provided in the path through which the pump light is propagated.

Although the description has been given to the example in which the tube pump 21 is used for the liquid circulating device in the embodiment, furthermore, it is also possible to use pumps of the other types. A pulsation is generated inmost of pumps. For this reason, there is a problem in that a vibration is applied to the stripe-shaped wave to be generated on the liquid film formed by the nozzle 26. According to the present embodiment, it is possible to suppress the superimposition of noises caused by the interference of the stripe-shaped wave appearing on the surface of the liquid film and the terahertz wave and to measure the true spectroscopic information of the liquid sample with high sensitivity regardless of the type of the pump to be used.

In addition, the embodiment is only illustrative for concreteness to carry out the present invention and the technical scope of the present invention should not be thereby construed to be restrictive. In other words, the present invention can be carried out in various configurations without departing from the gist or main features thereof.

EXPLANATION OF DESIGNATION

11 laser light spectral dispersing unit
12 terahertz wave generating semiconductor (terahertz wave light source)
13 terahertz wave spectral dispersing unit
14 terahertz wave focusing unit
15 terahertz wave detecting semiconductor (terahertz wave detecting unit)
16 variable optical delaying unit for time resolution
17 variable optical delaying unit for balance (variable optical delaying unit)
21 tube pump
22S sample liquid film generating unit
22R reference liquid film generating unit
26S, 26R nozzle
31S, 31R heating/cooling element
32 driving circuit
101 sample liquid film
102 reference liquid film

The invention claimed is:

1. A terahertz time domain spectroscopy device provided with a liquid sample in a path through which a terahertz wave is propagated and performing time domain spectroscopy measurement over a property of a terahertz wave transmitted through the liquid sample, comprising:
   a terahertz wave spectral dispersing unit for spectrally dispersing a terahertz wave to be generated from a terahertz light source into two waves;
   a terahertz wave focusing unit for focusing a terahertz wave transmitted through a sample liquid film provided in a path through which one of terahertz waves obtained by spectral dispersion through the terahertz wave spectral dispersing unit is propagated and a terahertz wave transmitted through a reference liquid film provided in a path through which the other terahertz wave obtained by the spectral dispersion through the terahertz spectral dispersing unit is propagated; and
   a terahertz wave detecting unit for detecting a terahertz wave focused by the terahertz wave focusing unit.

2. The terahertz time domain spectroscopy device according to claim 1 further comprising a viable optical delaying unit for variably setting a delay quantity of the terahertz wave in at least one of the path through which one of the terahertz waves is propagated and the path through which the other terahertz wave is propagated.

3. The terahertz time domain spectroscopy device according to claim 2 further comprising a liquid film moving unit for moving at least one of arrangement positions of the sample liquid film and the reference liquid film corresponding to movement of a reflection mirror possessed by the variable optical delaying unit.

4. The terahertz time domain spectroscopy device according to claim 3 further comprising:
   a laser light spectral dispersing unit for dispersing laser light emitted from a Femtosecond laser light source into two waves including pump light for operating the terahertz light source and sampling light for increasing weak current to be created by a terahertz wave incident on the terahertz wave detecting unit; and
   a variable optical delaying unit for time resolution which variably sets a delay quantity of the sampling light in a path through which the sampling light is propagated,
   the terahertz wave spectral dispersing unit and the terahertz wave focusing unit being provided in a path through which the terahertz wave to be generated by the terahertz wave light source corresponding to the pump light is propagated.

5. The terahertz time domain spectroscopy device according to claim 4 further comprising:
   a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

6. The terahertz time domain spectroscopy device according to claim 3 further comprising:

a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

7. The terahertz time domain spectroscopy device according to claim 2 further comprising:

a laser light spectral dispersing unit for dispersing laser light emitted from a Femtosecond laser light source into two waves including pump light for operating the terahertz light source and sampling light for increasing weak current to be created by a terahertz wave incident on the terahertz wave detecting unit; and a variable optical delaying unit for time resolution which variably sets a delay quantity of the sampling light in a path through which the sampling light is propagated, the terahertz wave spectral dispersing unit and the terahertz wave focusing unit being provided in a path through which the terahertz wave to be generated by the terahertz wave light source corresponding to the pump light is propagated.

8. The terahertz time domain spectroscopy device according to claim 7 further comprising:

a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

9. The terahertz time domain spectroscopy device according to claim 2 further comprising:

a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

10. The terahertz time domain spectroscopy device according to claim 1 further comprising:

a laser light spectral dispersing unit for dispersing laser light emitted from a Femtosecond laser light source into two waves including pump light for operating the terahertz light source and sampling light for increasing weak current to be created by a terahertz wave incident on the terahertz wave detecting unit; and a variable optical delaying unit for time resolution which variably sets a delay quantity of the sampling light in a path through which the sampling light is propagated, the terahertz wave spectral dispersing unit and the terahertz wave focusing unit being provided in a path through which the terahertz wave to be generated by the terahertz wave light source corresponding to the pump light is propagated.

11. The terahertz time domain spectroscopy device according to claim 10 further comprising:

a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

12. The terahertz time domain spectroscopy device according to claim 1 further comprising:

a pump;

a sample liquid film generating unit for generating the sample liquid film by using a measuring target liquid which is to be sent out by an action of the pump; and a reference liquid film generating unit for generating the reference liquid film by using a liquid for reference to be sent out by the action of the pump, wherein the sample liquid film generating unit and the reference liquid film generating unit include a vessel having a liquid tank, a pipe and a nozzle respectively, the pump sucking up a liquid through the pipe from the liquid tank, deriving the liquid sucked up to the nozzle through the pipe and jetting the liquid from the nozzle, thereby forming the sample liquid film and the reference liquid film, and further comprising a temperature control unit for applying a thermal disturbance to a liquid in the solution tank.

* * * * *